US00PP27432P2

(12) United States Plant Patent
Hansen

(10) Patent No.: US PP27,432 P2
(45) Date of Patent: Nov. 29, 2016

(54) ***SCHIZACHYRIUM* PLANT NAMED 'TWILIGHT ZONE'**

(50) Latin Name: *Schizachyrium scoparium*
Varietal Denomination: Twilight Zone

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 101 days.

(21) Appl. No.: 14/544,457

(22) Filed: Jan. 8, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Susan McCormick Ewoldt

(57) ABSTRACT

A new and distinct plant cultivar of little bluestem plant, *Schizachyrium scoparium* 'Twilight Zone' has a dense, upright habit with long arching foliage. Early foliage coloration becomes nearly a silvery mauve-purple by mid-summer that develops brighter purple highlights by early fall. The distal leaves continue up the culm to subtend the rachis in prominent fashion and produce a dense, full, foliar effect. The flowers remain effective with reddish-purple tinting into winter.

1 Drawing Sheet

STATEMENT REGARDING FEDERALLY SPONSORED RESEARCH

The present invention was supported in part by the U.S. Department of Agriculture. The U.S. Government therefore may have certain rights in the invention.

Botanical classification: *Schizachyrium scoparium.*
Varietal denomination: 'Twilight Zone'.

BACKGROUND OF THE INVENTION

The present invention relates to a new and distinct cultivar of *Schizachyrium scoparium* and will be referred to hereafter by its cultivar name. 'Twilight Zone', the "new cultivar" and "the new plant." 'Twilight Zone' represents a new cultivar of little bluestem, an ornamental grass grown for landscape use. The new plant was a selection of the United States Department of Agriculture germplasm Germplasm Resources Information Network Accession PI 216767 H-V 265.

The inventor initially selected the new cultivar, in a full-sun trial field of a wholesale nursery in Zeeland, Mich., USA. The seedling was selected among several thousand other seedlings collected from open pollinations of numerous cultivars and selections. Prior to planting in the open field the seedlings were greenhouse grown in plugs in the same nursery in Zeeland, Mich. in 2011. Preliminary evaluation was in the fall of 2011, and final evaluation and selection of 'Twilight Zone' was performed in fall of 2013.

*Schizachyrium scoparium* 'Twilight Zone' has been successfully propagated by culm division at the same nursery in Zeeland, Mich. since the spring of 2011 and since 2012 by sterile plant tissue culture shoot division. The result asexually propagated plants have remained stable and true to type for all traits of the original plant in successive generations.

BRIEF SUMMARY OF THE INVENTION AND COMPARISON

The following traits have been repeatedly observed and represent the characteristics of the new cultivar which in combination distinguish *Schizachyrium scoparium* 'Twilight Zone' from all other little bluestem plants known to the inventor:

1. Early foliage coloration of nearly a silvery mauve-purple cast beginning in mid-summer.
2. Early fall foliage develops brighter purple highlights.
3. Dense upright habit with long arching foliage.
4. Distal leaves continuing up culm to subtend rachis in prominent fashion.
5. Late-flowering rachis with reddish purple tinting which remains effective into winter.

*Schizachyrium scoparium* 'Twilight Zone' compares most closely with the little bluestem cultivars 'Carousel' U.S. Plant Pat. No. 20,948, 'Prairie Munchkin' U.S. Plant Pat. No.26,335 and 'Blaze' (not patented). The parents of the new plant are unknown, so no comparisons are possible.

Compared to 'Carousel' the new plant has denser foliage, is taller and develops the reddish purple foliation earlier. Compared to 'Blaze', the new plant is taller, with denser foliage and develops more purple in the foliage and has less orangish-red. 'Twilight Zone' also flowers later than either of the nearest comparison cultivars. Compared to *Schizachyrium* 'MinnblueA' U.S. Plant Pat. No. 17,310, the new plant is much taller and more purple with less blue-green in the foliage earlier in the season.

The comparison below in Table 1 shows a more succinct differentiation between other known little bluestem cultivars.

TABLE 1

| *Schizachyrium* Cultivars | Height | Foliage color | Habit |
|---|---|---|---|
| 'Blaze' | 90 cm | orangish-red | upright compact |
| 'Carousel' | 75 cm | mahogany | upright compact |
| 'MinnblueA' | 120 cm | burgundy tipped blue | upright tall |
| 'Prairie | 75 cm | maroon with orange | tight compact |

TABLE 1-continued

| *Schizachyrium* Cultivars | Height | Foliage color | Habit |
|---|---|---|---|
| Munchkin' | | | column |
| 'Twilight Zone' | 112 cm | silvery mauve purple | upright arching |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color. The plant in the photographs is a three-year old plant grown in a full-sun trial garden in Zeeland, Mich., USA with supplemental water and minimal fertilizer when needed.

DETAILED BOTANICAL DESCRIPTION

Figure 1:
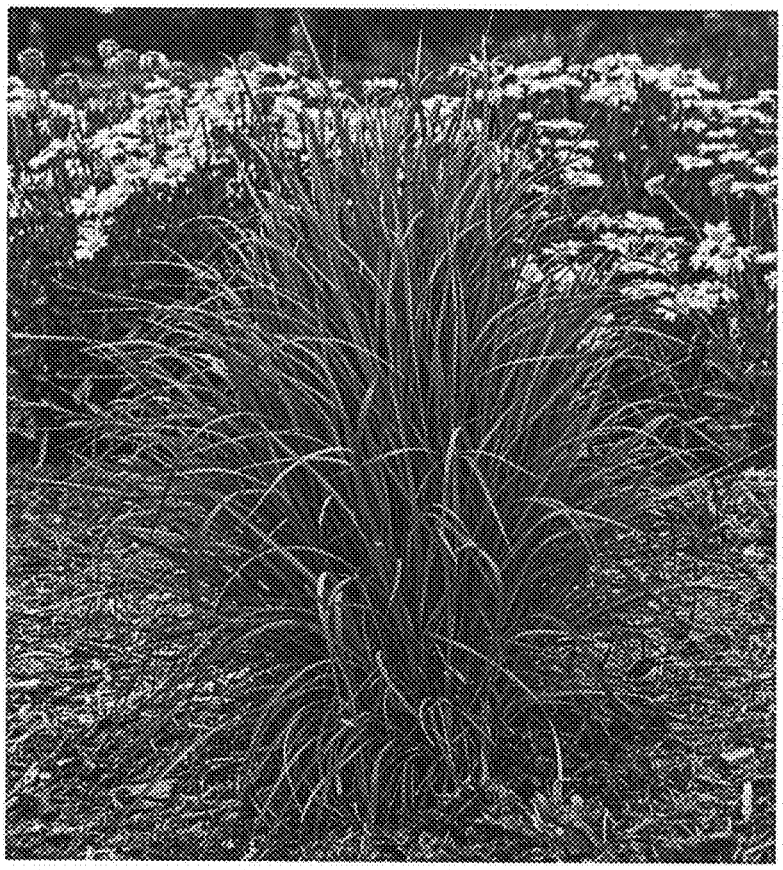
FIG. 1 shows the plant habit and foliage in mid-summer.
Figure 2:
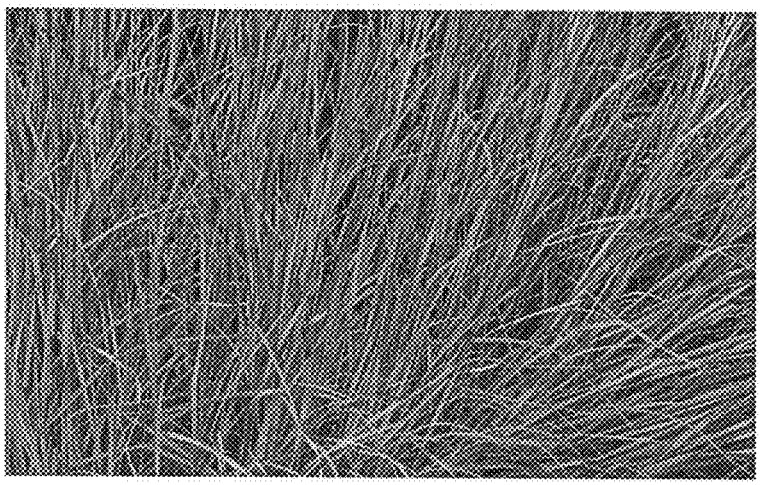
FIG. 2 shows a close-up of the foliage in late-fall.

The following detailed description of *Schizachyrium scoparium* 'Twilight Zone' are of taken from a three-year old plant grown in a full-sun trial field with supplemental water and fertilizer in Zeeland, Mich. The color references are in accordance with the 2001 edition of The Royal Horticultural Society Colour Chart except where common color terms of ordinary dictionary reference are used. The phenotype may vary slightly with different environmental conditions, such as temperature, light, fertility, moisture and maturity levels, but without any change in the genotype.

Female parentage: Unknown.

Male parent: Unknown.

Growth rate: Rapid, finishing in 65 mm container from a stage 3 tissue culture plant in two and a half to three months; producing roots in tissue culture in three to four weeks.

Rooting habit: Normal, branching; fibrous, wiry, deep rooted up to about 90 cm long; color of roots near white to tan depending on soil type.

Plant habit: Herbaceous perennial grass, compact with upright culms and dense arching foliage.

Plant size: About 112 cm tall and about 75 cm wide.

Culm: Round in cross section; thin, wiry, strong; glaucous, glabrous; with foliage to near distal end; to about 112 cm long, average about 106 cm long and 2.5 cm near base; about 4.0 to 6.0 cm of culm exposed between leaves.

Culm color: Seasonally and position variable: summer nearest RES 138A, fall from between RHS 183A and RHS 187B and winter drying to between RHS 177D and RHS 164D; of exposed area between leaves.

Nodes: About nine per culm; swollen to about 5.0 diameter of lower nodes; glabrous, glaucous; internode length between about 18.5 cm on lower internodes and about 2.5 in distal internodes, average about 8.0 cm.

Node color: Nearest RHS 187A by mid-summer and into winter.

Foliage: Leaves flat, alternate, linear, entire, glabrous, glaucous; apex narrowly acute, base sheathing and usually open with long split extending to near node; sheath portion up to 14.0 cm long on lowest leaves and 4.0 cm on upper leaves; largest leaves about 51.0 cm long and about 4.5 mm wide; upper leaves about 8.5 cm long and about 2.0 mm across; six to eleven leaves per culm.

Foliage color: Varies with season; on adaxial summer between RHS 138A and RHS 138B, and abaxial nearest RHS 138C; mid-summer developing from the apex proximally to the culm between RHS N187B and RHS N187A on adaxial and abaxial nearest RHS N187B; fall color nearest RHS N187B on adaxial and RHS N187B on abaxial; winter color adaxial nearest RHS 177B with abaxial lighter than RHS 177D.

Venation: Parallel.

Vein color: Same as surrounding tissue of both abaxial and adaxial.

Ligule: Membranous, fringed apex, about 2.0 mm long and width equal to leaf.

Ligule color: Between RHS 177D and RHS 165B.

Flower description: Branched raceme at distal five to seven nodes; flower period late fall in Western Michigan; remaining effective into winter.

Rachis: Glaucous, glabrous; up to about 15.0 cm long, and about 0.5 mm diameter; average about 12.0 cm long and 0.5 mm diameter; frequently with two or three rachis per node.

Rachis color: Variable depending on season and light exposure, nearest RHS 165C with less light exposure and between RHS N187B and RHS N187A with more light exposure.

Spikelets: In pairs adpressed to rachis; one sessile and one pedicellate; pedicellate spikelet sterile and reduced; sessile spikelet fertile, about 16.0 mm long and about 15.0 mm across.

Glumes: Paired; lemma surrounding inner palea; acute apex; adhering to caryopsis; color nearest.

Lemma: About 7.0 mm long and about 1.0 mm wide; acute apex, color nearest RHS N199C.

Palea: About 6.0 mm long and about 1.0 mm wide; acute apex; color nearest RHS N170B.

Awn: Long, thin, nearly hair-like, with membranous base; about 15.0 mm long and base of about 0.5 mm wide, apex about 0.1 mm wide; color between RHS 165A and RHS 165B above the translucent membranous base.

Spikelet hairs: About 3.0 mm long and less than 0.1 mm diameter; collective color nearest RHS N155D.

Reproductive:

*Androecium*.—Usually three; Anther: oblong; basifixed; about 3.0 mm long and about 0.5 mm diameter; color nearest RHS 187B; Filament: very fine, about 0.2 mm diameter and about 2.0 mm long; color nearest RHS 155D; Pollen; abundant; color nearest 187B.

*Gynoceium*.—One; Style: plumose, about 2.5 mm long and about 1.0 mm diameter; color nearest RHS 186D; Stigmas: numerous, non-secund, surrounding style; color nearest RHS 187D.

Seed: Caryopsis; enclosed in glume; ovoid with broadly acute apex; less than 1.0 mm long and 0.7 mm diameter; color varies with maturity between RHS 200C and RHS N199D.

Pest and disease resistance: Generally free of pests and diseases, susceptibility or resistance beyond that typical of little bluestem has not been observed.

Hardiness: Hard from U.S.D.A. zones 3 to 9; able to withstand adverse weather and still remain upright; like most little bluestem the new plant is able to withstand some drought once established.

I claim:

1. A new and distinct ornamental cultivar of little bluestem plant, *Schizachyrium scoparium* plant named 'Twilight Zone', as herein described and illustrated, for landscaping the garden en masse or individually.

* * * * *